United States Patent
Dauner et al.

(10) Patent No.: US 6,773,459 B2
(45) Date of Patent: Aug. 10, 2004

(54) MEDICAL, BIORESORBABLE IMPLANT, PROCESS FOR ITS PRODUCTION AND THE USE THEREOF

(75) Inventors: Martin Dauner, Esslingen (DE); Helmut Hierlemann, Goeppingen (DE); Heinrich Planck, Nuertingen (DE); Lutz Claes, Sommerweg 5, 89233 Neu-Ulm (DE); Lutz Duerselen, Neu-Ulm (DE); Anita Ignatius, Elchingen (DE)

(73) Assignees: Deutsche Institute fuer Textil-und Faserforschung Stuttgart Stiftung des oeffentlichen Rechts, Denkendorf (DE); Lutz Claes, Neu-Ulm (DE)

( * ) Notice: Subject to any disclaimer, the term of this patent is extended or adjusted under 35 U.S.C. 154(b) by 0 days.

(21) Appl. No.: 09/950,048

(22) Filed: Sep. 12, 2001

(65) Prior Publication Data

US 2002/0062152 A1 May 23, 2002

(30) Foreign Application Priority Data

Sep. 15, 2000 (DE) .......................................... 100 46 119

(51) Int. Cl.$^7$ ................................................. A61F 2/08
(52) U.S. Cl. ................................ 623/13.18; 623/13.19; 623/13.2
(58) Field of Search ..................... 623/1.1, 1.38–1.54, 623/11.11, 12, 13.11–13.2, 23.75–23.76, 66.1; 606/151, 153–158, 228–231, 36

(56) References Cited

U.S. PATENT DOCUMENTS

| | | | |
|---|---|---|---|
| 4,917,699 A | * 4/1990 | Chervitz | 623/13.19 |
| 4,932,972 A | * 6/1990 | Dunn et al. | 623/13.19 |
| 4,942,875 A | * 7/1990 | Hlavacek et al. | 606/230 |
| 5,024,669 A | * 6/1991 | Peterson et al. | 623/13.14 |
| 5,578,046 A | 11/1996 | Liu et al. | |
| 6,113,640 A | * 9/2000 | Tormala et al. | 623/18.11 |
| 6,458,148 B1 | * 10/2002 | Dauner et al. | 606/228 |

FOREIGN PATENT DOCUMENTS

| | | |
|---|---|---|
| DE | 25 15 970 | 10/1975 |
| DE | 38 01 426 | 8/1989 |
| DE | 38 30 005 | 11/1989 |
| DE | 38 30 481 | 3/1990 |
| DE | 40 12 602 A1 | 10/1991 |
| DE | 40 12 602 C2 | 10/1991 |
| DE | 196 13 730 | 10/1997 |
| DE | 196 41 334 | 4/1998 |
| DE | 197 21 876 | 11/1998 |
| DE | 198 33 796 | 2/2000 |
| DE | 199 06 172 | 7/2000 |
| DE | 199 12 360 | 9/2000 |
| DE | 199 12 648 | 9/2000 |
| EP | 0 239 775 | 10/1987 |
| EP | 0 241 252 A2 | 10/1987 |
| EP | 0 241 252 B1 | 10/1987 |
| EP | 0 272 902 | 6/1988 |
| EP | 0 452 807 | 10/1991 |
| EP | 0 645 149 | 3/1995 |
| EP | 0 677 297 | 10/1995 |
| EP | 1 038 540 | 9/2000 |
| EP | 1 099 421 | 5/2001 |
| WO | WO 88/06872 | 9/1988 |
| WO | WO 9641596 A1 * | 12/1996 ............. A61F/2/30 |
| WO | WO 97/11724 | 4/1997 |
| WO | WO 99/51163 | 10/1999 |

OTHER PUBLICATIONS

Dauner, Martin, et al., "Ligament Replacement Polymers: Commercial Products".

Dauner, Martin, et al., "Ligament Replacement Polymers: Technological and Design Aspects".

* cited by examiner

*Primary Examiner*—David J. Isabella
*Assistant Examiner*—Urmi Chattopadhyay
(74) *Attorney, Agent, or Firm*—Nath & Associates PLLC; Marvin C. Berkowitz; Derek Richmond

(57) ABSTRACT

A medical, bioresorbable implant, particularly for cruciate ligament augmentation, is constructed as a composite structure in textile construction from at least two biocompatible polymer materials, which differ in their chemical composition and/or polymer structure and which are degradable, the implant having a predetermined initial tensile stiffness and a different degradation behaviour of the polymers and/or the textile construction is selected in such a way that the tensile stiffness decreases during degradation.

12 Claims, No Drawings

MEDICAL, BIORESORBABLE IMPLANT, PROCESS FOR ITS PRODUCTION AND THE USE THEREOF

DESCRIPTION

The present invention relates to a medical, bioresorbable implant, a process for its production and its use in medicine.

Artificial implants are generally used in surgery as means for fixing, supporting or replacing diseased or injured body parts. For example, surgical sutures, replacements for tendons and ligaments and vascular prostheses are known.

Artificial implants in the form of cords or bands have been specifically developed for applications in orthopedic surgery for humans and animals. A typical example of the use thereof is a cruciate ligament rupture, where an implant is useful in reconstruction or as a prosthesis.

As implants of non-resorbable materials suffer from significant disadvantages, such as e.g. foreign body reactions and an infection tendency, implants of partly or completely resorbable material have been developed. The Ethicon DE-A1-19613730 discloses a flat or areal implant of not or only slowly resorbable material, which is stiffened with a further, rapidly resorbable material. Various degradable implants based on alpha-hydroxycarboxylic acid polyesters are also known. In DE-C2-4012602, Ethicon discloses polydioxanone cords.

Particularly in applications where the implant is only intended to temporarily exercise its function until the endogenic tissue has recovered, it is desirable for the inserted implant to gradually lose its mechanical stability and consequently increasingly transfer the load to the tissue to be restored.

In practice the known implants suffer from the disadvantage that during the degradation phase, following an initial softening, an embrittlement occurs, which reduces the extensibility of the implant and either leads to an undesired extension restriction or to premature implant fracture. The functional loading is only taken over in the known implants by the endogenic tissue to be restored when the implant material has degraded to such an extent that implant fracture occurs.

BRIEF SUMMARY OF THE INVENTION

The problem of the invention is consequently to make available a medical, bioresorbable implant, particularly an augmentate, which has in vivo the desired mechanical characteristics together with an advantageous biological degradation and resorption behaviour, which is simple and inexpensive to manufacture and which is easy and reliable during use for implantation purposes during surgery.

This problem is solved by a medical, bioresorbable implant, particularly for cruciate ligament augmentation, constructed as a composite structure with a textile construction from at least two biocompatible polymer materials, which differ in their chemical composition and/or polymer structure and which are degradable, the implant having a predetermined initial tensile stiffness and a differing degradation behaviour of the polymers and/or the textile construction is selected in such a way that the tensile stiffness decreases during degradation.

The implant is particularly constructed as an augmentate for cruciate ligament augmentation. As a result of the decrease of the tensile stiffness of the implant, increasingly the load is transferred to the tissue to be restored.

In this connection stiffness is a measure of the resistance to shape changes. It can be represented as an increase in the force pattern over the displacement. It is also related to the modulus of elasticity, which additionally takes account of the starting cross-section and starting length of the sample material.

In the biological resorption of natural or synthetic polymer materials in a physiological environment, there is firstly a degradation of the polymer chains, followed by a further decomposition of the degradation products and finally the substance mass is resorbed. A decrease in the tensile stiffness of the polymer can occur during degradation, but at the latest during the resorption of the decomposition products.

In a special embodiment a medical, bioresorbable implant is made available, which is constructed as a composite structure in textile construction from at least three or more, biocompatible polymer materials, which differ as regards their chemical composition and/or polymer structure and which are degradable, the implant having a predetermined initial tensile stiffness and a differing degradation behaviour of the polymers and/or the textile construction is selected in such a way that the tensile stiffness decreases during degradation. As a rule two or three different polymer materials are sufficient.

TITLE OF THE INVENTION

With particular advantage the implant according to the invention is characterized in that all the polymers are completely resorbable.

DETAILED DESCRIPTION OF THE INVENTION

According to the invention the decrease in the tensile stiffness of the implant can result from the textile construction and the degradability of at least two of the polymers.

The implant can have an initial tensile stiffness in the range 50 to 250 N/mm, particularly 80 to 160 N/mm, based on an implant length of 100 mm. The implant material stiffness is not only related to the cross-section and the stiffness can in particular decrease with a reducing cross-section. Advantageously the implant according to the invention is characterized in that its tensile stiffness-causing components are formed from at least partly crystalline polymers. The tensile stiffness of the implant can have a half-life in vitro and in vivo of 3 to 9 months, particularly 5 to 7 months.

In an embodiment of the implant according to the invention at least one high stiffness polymer can have a faster degradability than at least one further polymer with a lower stiffness. In a special embodiment of the implant according to the invention the different polymers can have a roughly identical stiffness, but a differing degradation behaviour.

According to the invention, a slowly resorbable polymer can have a resorption time in vivo of 6 to 36 months, particularly 12 to 24 months. A rapidly degrading polymer can have a degradation time in vivo of 3 to 36 weeks, particularly 12 to 26 weeks. A polymer material rapidly degrading in this way rapidly loses its strength, but is still present in the implant. The load hitherto taken over by a rapidly degrading component, is now taken over by other components of the implant and/or by the natural body tissue. Thus, as a result of the partial biological decomposition of polymer material in the implant successively space is created for the endogenic tissue which is subsequently growing and in fact before the entire implant strength is lost. The known prior art implants suffered from the disadvantage that firstly the strength was lost, followed by polymer mass loss by resorption.

The half-life periods of the degradation of the different polymers in the implant according to the invention can be matched to one another in such a way that, particularly after a plateau phase, the implant stiffness decrease is as constant as possible over the implant degradation time. Advantageously the half-life of a more slowly degrading component can be 25 to 100%, preferably 50 to 80% longer than that of the more rapidly degrading component. When using three or more polymer components the grading of the half-life periods can be correspondingly adapted. The polymer degradation behaviour can be influenced by the chemical composition and structure thereof, e.g. by a content of monomer or oligomer components. Another influencing factor through the variation of which it is possible to modify the decomposition behaviour of the polymer according to the invention, is the intensity and duration of gamma radiation, such as e.g. takes place for the purpose of sterilizing medical material.

According to the invention, the more slowly degrading material preferably takes up a larger or identical volume in the implant to other materials, so as in this way to ensure an adequate strength.

The distribution of the degradation and resorption of the different polymers in the implant according to the invention over a longer period of time can be characterized by a further advantage in that in particular in the case of alpha-hydroxycarboxylic acid polyesters, a smaller monomer quantity per unit of time is delivered to the body tissue, which prevents overacidification of the surrounding tissue and consequently aids healing.

In the implant according to the invention the textile construction can be constructed in such a way that through the degradation of one material, the structure of at least one further material acquires a higher extensibility. This is e.g. the case with a mixed braid of fibres degrading at different speeds.

In a special embodiment of the implant it can have in the textile construction at least one polymer material serving as a mechanical barrier, which is more rapidly degradable than at least one further polymer. According to the invention, the barrier material can in particular be a filling material. Filling material provided in the implant according to the invention can e.g. be a core. Advantageously the filling material is in particular constructed as a solid material. In a special embodiment of the invention the filling material does not require inherent stiffness. The filling material can e.g. be a polymer with a largely amorphous structure. An impregnation of a braided or knitted fabric can also serve as an initial extension barrier.

In a preferred embodiment of the invention the barrier material can be a load-absorbing, i.e. tensile strength-absorbing material, which relieves a less stiff construction and/or an initially less stiff polymer material. Advantageously, by removing and in particular degrading a load-absorbing material, the textile construction acquires a higher extensibility and/or a less stiff polymer material can absorb the load. This is e.g. the case with a braid, which has axial standing threads of a stiff material and which is relatively rapidly degradable. The initially still relieved braided structure then increasingly absorbs the load, accompanied by a simultaneous extension.

The extensibility of the implant according to the invention is to be matched to the intended area of application. The absolute linear expansion of the implant should not exceed the natural elasticity of the body part to be supported, e.g. the tendon or ligament. Preferably it is identical to the natural elasticity.

The implant according to the invention is advantageously characterized in that it is formed from polymer material in the form of filaments. In particular, the textile construction can at least partly be formed by filaments. The filaments can be both single filaments and multifilaments. In an embodiment of the invention the filaments can be formed in each case from a single polymer material. In a preferred embodiment the filaments are in the form of multicomponent fibres, particularly bicomponent fibres. In addition, the multifilaments can be formed from a mixture or blend of filaments of different polymer materials. Advantageously filaments in the implant can have a diameter of 6 to 30 $\mu$m, particularly 10 to 17 $\mu$m. Polymer filaments can be stretched and thermally after-treated using known procedures in order to obtain optimum fibre characteristics for use. As is known to the experts, a stretching process aids the orientation of the polymer molecules in the filament and the formation of crystalline structural features. As a result of the correlation of structure and characteristics in polymers, the tensile stiffness of the polymer fibres can be influenced via the degree of stretching.

The implant according to the invention is preferably constructed in such a way that at least part of the filaments is textured. A texturing of filaments in the implant according to the invention can be performed according to conventional procedures and in particular the filaments can be soldered or doubled. In an embodiment of the invention the more rapidly degrading filaments can be textured. In a preferred embodiment the more slowly degrading filaments can be textured. Textured fibres in the implant can favourably influence extensibility. In addition, textured fibres can aid a growing in of natural body tissue.

According to an embodiment of the invention the composite structure can have a linear construction in the implant, particularly in the form of a strand, string, cord, strip or wire. Such an embodiment can be used with particular advantage for surgical treatment on tendons and ligaments of a human or animal patient.

In a special embodiment of the invention, in the implant the composite structure can be constructed in the form of a fabric. Such a flat embodiment is particularly advantageous for use as a hernia net. In a preferred embodiment of the invention, in the implant the composite structure can be branched. Such an embodiment is particularly suitable for use e.g. in the anterior cruciate ligament.

In another special embodiment of the invention, in the implant the composite structure can be a three-dimensional body. Such an embodiment is e.g. particularly advantageous for use in osteosynthesis.

A composite structure can in particular be in single-layer form. An example for such a composite structure is a braid of a yarn blend.

Preferably a composite structure is constructed in multilayer form. An example of a multilayer composite structure according to the invention are two telescoped tubes.

According to the invention, in the implant the composite structure can be formed using a single textile technology. Preferably the composite structure is formed in a combination of textile technologies.

In an embodiment the composite structure can at least partly be in the form of a woven construction, particularly with warp yarns in the longitudinal direction.

In a special embodiment the composite structure can at least partly be constructed as knitwear, particularly as a knitted construction.

In a preferred embodiment the composite structure can at least partly be constructed as a braided construction, particularly as a spiral braid. In a particularly preferred embodiment the spiral braid can be constructed with standing fibres of elastomer material. In a further development the composite structure can at least partly be constructed as a three-dimensional braid. In another special embodiment a braid can be formed from bicomponent fibres and in particular the more rapidly degrading components envelop the more slowly degrading component.

In a particularly preferred embodiment the implant can at least partly be constructed as a core-envelope-composite structure, preferably with at least two envelopes.

Advantageously the textile design of the implant is such that polymer fibres are not mainly arranged in the direction of the longitudinal axis of the implant, but at an angle between 5 and 60° (radians) to the longitudinal axis. This permits a structural extension and in the case of the degradation and resorption of a polymer component a stiffness decrease of the complete system can be obtained. As a result during the degradation phase the stiffness of the implant successively decreases, as does the strength, but the rupture strain is roughly maintained. For an optimum success of the treatment the residual stiffness should still be high enough to ensure that there is no overstretching of the natural body tissue, such as a tendon or a ligature. Therefore the implant can assist the regenerating body tissue up to the late resorption phase without excessively relieving the same and in this way aids the full functioning capacity of the regenerated tissue. In the healing phase the implant can absorb unphysiologically large deformations.

Particularly for the treatment of cruciate ligaments preference is given to an implant in the form of a braid in a correspondingly constructed composite structure. An implant in the form of a braid has a structural extension advantageous for such an application.

The present invention also relates to a process for the production of a medical, bio-resorbable implant, particularly for cruciate ligament augmentation, characterized in that two or more biocompatible polymer materials having a different chemical composition and/or polymer structure and which are degradable are used and at least two of the composite components differ in their degradation behaviour and using textile processing methods at least one polymer material is shaped into a composite structure in such a way that it acquires a predetermined initial tensile stiffness and the implant stiffness decreases during degradation.

The invention also relates to the use of the medical implant according to the invention in surgery, particularly for cruciate ligament augmentation.

For the use as an augmentation cord, it is advantageous if over a period of time there is a decrease in the stiffness of the artificial implant compared with the natural endogenic material Decreasing stiffness can take place elastically at the outset or as a result of simple (tension-free) lengthenability, e.g. in the case of a mixed fibre braid following degradation and resorption of a fibrous material.

For use as a hernia net this leads to the production of scar tissue taking over the function of fasciae. Here again a degrading stiffness is desired.

For optimum use, an implant according to the invention can be combined with structures, which are e.g. used for anchoring in the body of the patient, such as rings. It is also possible to combine adjuvants and/or medical substances with the implant in order to assist the success of the treatment.

Further features and details of the invention can be gathered from the following description of preferred embodiments in example form. The individual features can be implemented singly or in the form of combinations. The examples serve merely to illustrate the present invention, which is in no way restricted thereto.

EXAMPLE 1

Comparison of the Characteristics of Bioresorbable Polymers

The following table provides information on the physical and mechanical characteristics, together with the degradation and resorption behaviour of different biocompatible polymers based on glycolide, lactide and hydroxycarboxylic acid.

Degradation/resorption data

| Polymer | Melting range (° C.) | Tg point (° C.) | Process temperature (° C.) | Fibre tensile strength (MPa) | Degradation weeks | Resorption weeks |
| --- | --- | --- | --- | --- | --- | --- |
| Polyglycolic acid (PGA) | 215–226 | 36 | 230–260 | 760–920 | 4–5 | 7–20 |
| Poly-L-lactide (P-L-LA) | 175–180 | 55–60 | 180–230 | 600–800 | 16–52 | |
| Poly-D-lactide (P-D-LA) | | | | | | 40 → 104 |
| Poly-DL-lactide (P-DL-LA) | amorphous | 50 | 150–190 | 250–350 | 15–30 | 25–52 |
| Poly-L/DL-lactide 70:30 P-L/DL-LA 70:30 | amorphous | 52 | 170–200 | 300–450 | 18–36 | 36–60 |
| Poly-(glycolide-co-L-lactide) 90/10 VICRYL ® | 198 | 36–45 | 200–250 | 570–910 | 4–5 | 13–18 |
| Poly-(L-lactide-co-glycolide) ("LGA 90/10") | 156 | 54 | 180–220 | 500–750 | 10–20 | 30–52 |
| Poly-β-hydroxycarboxylic acid | 175 | 5 | >190 | n.a. | 25–75 | 50–100 |

EXAMPLE 2

Production of a Two-Layer Braid of Fibre Blends

Yarns of the copolymers poly-L-lactide-co-glycolide in a monomer ratio 10:90 (LGA 1090), poly-L-lactide-co-glycolide in the monomer ratio 90:10 (LGA 9010) and poly-L-lactide (P-L-LA) with a fineness of in each case approximately 330 dtex are doubled. They are processed with eight bobbins to a core braid, which is enveloped with an envelope from the same yarn blend with 16 bobbins. The initial strength is 655 N at 17% rupture strain. Stiffness decreases degressively from 116 N/mm over a 12 month period towards 0.

EXAMPLE 3
Production of a Two-Layer Braid of Different Polymer Materials

A core braid of rapidly degrading LGA 1090 (8 bobbins× 800 dtex) is braided with a 16 bobbin braid of more slowly degrading LGA 9010 and P-L-LA, in each case of 840 dtex, in each case 8 bobbins being loaded with a material. The initial strength is 529 N for 17% rupture strain. The course of the stiffness over the degradation time is qualitatively comparable to that of example 1, but the initial stiffness is 95 N/mm and the gradient is smaller.

EXAMPLE 4
Production of a Two-Layer Braid of Different Polymer Materials

A core braid of more slowly degrading PLLA (8 bobbins× 800 dtex) is braided with a 16 bobbin braid of somewhat more rapidly degrading LGA 9010 (840 dtex). The initial strength is 632 N for 18% rupture strain. There is a stepwise course of the stiffness over the degradation time. The rupture strain remains constant for a long time, but the strength decreases. This construction has the advantage that the more rapidly degrading component is on the outside and consequently degradation products are more rapidly absorbed by the body fluid during degradation.

EXAMPLE 5
Triple Braid

A triple braid is formed from the inside to the outside: LGA 1090 (8 bobbins×960 dtex), LGA 9010 (12 bobbins× 960 dtex) and P-L-LA (24 bobbins ×960 dtex), only one yarn material being used per braid layer. The degradation speed decreases from the inside to the outside. The initial strength is 551 N with a 12% rupture strain and the stiffness decreases almost linearly from 145 N/mm.

EXAMPLE 6
Triple Core-Envelope Construction

A triple construction is constructed from a monofilament core of a degradable glycolic acid/trimethylene carbonate copolymer 55:45, braided with LG 9010 (12 bobbins×960 dtex) and as the external envelope P-L-LA (24 bobbins×960 dtex). For an initial strength of 481 N and 13% rupture strain, the stiffness progressively decreases here from 123 N/mm over 12 months.

What is claimed is:

1. Medical, bioresorbable ligament augmentate wherein
   the augmentate has a textile, at least partially braided, construction selected from the group consisting of strand, string, cord, band and wire
   and has a composite structure from at least two biocompatible polymer filaments and the filaments are degradable and differ in at least one characteristic consisting of their chemical composition and polymer structure
   and the ligament augmentate has a predetermined initial tensile stiffness and,
   the different degradation behaviour of the polymers and the textile braided construction are selected in such a way that the tensile stiffness decreases during degradation of the ligament augmentate and
   wherein a slowly resorbable polymer has a resorption time in vivo of 6 to 36 months and a rapidly degrading polymer has a degradation time in vivo of 3 to 36 weeks and
   wherein the ligament augmentate has an initial tensile stiffness with a half-life in vitro and in vivo of 3 to 9 months in the range 50 to 250 N/mm. based on an implant length of 100 mm.

2. Ligament augmentate according to claim 1, wherein the ligament augmentate has an initial tensile stiffness in the range 80 to 160 N/mm.

3. Ligament augmentate according to claim 1, wherein the ligament augmentate's tensile stiffness has a half-life in vitro and in vivo of 5 to 7 months.

4. Ligament augmentate according to claim 1, wherein the textile braided construction is constructed in such a way that through the degradation of one material, the structure of at least one further material acquires a higher extensibility.

5. Ligament augmentate according to claim 1, wherein the textile braided construction contains at least one polymer material serving as a mechanical barrier and which is more rapidly degradable than at least one further polymer.

6. Ligament augmentate according to claim 5, wherein a barrier material is a load-absorbing material, which relieves at least one member of the group consisting of a less stiff construction and a less stiff polymer material.

7. Ligament augmentate according to claim 1, wherein at least two filaments are combined to form multifilaments from a mixture of filaments of different polymer materials.

8. Ligament augmentate according to claim 1, wherein the composite structure is at least partly constructed as a three-dimensional braid.

9. Ligament augmentate according to claim 1, wherein the composite structure is at least partly constructed as a core-envelope-type composite structure, which has at least two envelopes.

10. Ligament augmentate according to claim 1, which is used as an implant for surgery.

11. Ligament augmentate according to claim 1, which is used as an implant for cruciate ligament augmentation surgery.

12. Process for the production of a medical bioresorbable ligament augmentate, wherein two or more biocompatible and degradable polymer filaments differ in at least one feature consisting of chemical composition and polymer structure and wherein a slowly resorbable polymer has a resorption time in vivo of 6 to 36 months and a rapidly degrading polymer has a degradation time in vivo of 3 to 36 weeks are braided to a composite structure by the use of textile processing methods in such a way that the ligament augmentate acquires a predetermined initial tensile stiffness with a half-life in vitro and in vivo 3 to 9 months in the range 50 to 250 N/mm, based on an implant length of 100 mm and wherein the at least two filaments differ in their degradation behaviour and the stiffness of the ligament augmentate decreases during degradation.

* * * * *